(12) United States Patent
Kandori et al.

(10) Patent No.: US 6,269,262 B1
(45) Date of Patent: Jul. 31, 2001

(54) BIOMAGNETIC FIELD MEASURING APPARATUS

(75) Inventors: Akihiko Kandori, Hachioji; Keiji Tsukada, Kashiwa; Ryuichi Shinomura, Higashimatsuyama; Hiroyuki Suzuki, Hitachinaka; Hitoshi Sasabuchi, Mito; Shoji Kondo, Hitachinaka; Yasuaki Komiyama, Hitachinaka; Kenji Teshigawara, Hitachinaka, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/094,690

(22) Filed: Jun. 15, 1998

(30) Foreign Application Priority Data

Jun. 20, 1997 (JP) .................................... 9-163741
Sep. 18, 1997 (JP) .................................... 9-252960

(51) Int. Cl.⁷ ....................................................... A61B 5/05
(52) U.S. Cl. ........................ 600/409; 600/425; 600/481; 600/508; 600/511; 600/513; 600/514; 324/248; 324/260; 324/262
(58) Field of Search ................................... 600/407, 404, 600/425, 481, 508, 512, 513, 523, 524, 437, 440, 444, 450, 509, 511, 443

(56) References Cited

U.S. PATENT DOCUMENTS

| | | | |
|---|---|---|---|
| 5,265,611 | 11/1993 | Hoenig et al. | 128/653.1 |
| 5,432,544 | * 7/1995 | Ziarati | 348/61 |
| 5,464,014 | * 11/1995 | Sugahara | 128/653.2 |
| 5,509,421 | 4/1996 | Muller et al. | 128/662.04 |
| 5,532,592 | 7/1996 | Colclough | 324/248 |
| 5,846,198 | 12/1998 | Killmann | 600/424 |
| 5,879,297 | 3/1999 | Haynor et al. | 600/407 |

FOREIGN PATENT DOCUMENTS

| | | |
|---|---|---|
| 60-21740 | 4/1985 | (JP) . |
| 5-212008 | 8/1993 | (JP) . |
| 6-254172 | 9/1994 | (JP) . |
| 6-269426 | 9/1994 | (JP) . |
| 6-335465 | 12/1994 | (JP) . |
| 7-308303 | 11/1995 | (JP) . |
| 8-24298 | 1/1996 | (JP) . |
| 8-56927 | 5/1996 | (JP) . |

OTHER PUBLICATIONS

Japanese Journal of Magnetic Resonance in Medicine, vol. 14, Supplement, (1994), pp. 471–474.
Gyroscan ACS–NT, the ultra compact 1.5T MR system, Phillips Medical Systems.
Review of Scientific Instruments, vol. 66, No. 10, Oct. 1995, "Multichannel SQUID system detecting tangential components of the cardiac magnetic field", K. Tsukada et al, pp. 5085–5091.

* cited by examiner

Primary Examiner—Peter Vo
Assistant Examiner—Jeoyuh Lin
(74) Attorney, Agent, or Firm—Mattingly, Stanger & Malur, P.C.

(57) ABSTRACT

A biomagnetic field measurement apparatus includes a bed which holds a subject to be inspected in a shielded room. A cryostat holds a plurality of SQUID magnetometers at low temperature. The cryostat is arranged in the shielded room and the plurality of SQUID magnetometers detect a magnetic field generated from the subject. A driving and detecting circuit drives the plurality of SQUID magnetometers and detects signals therefrom that are processed by a computer. A display that is arranged in the shielded room displays data for viewing by an operator.

3 Claims, 12 Drawing Sheets

BIOMAGNETIC FIELD MEASURING APPARATUS

BACKGROUND OF THE INVENTION

The present invention relates to a biomagnetic field measuring apparatus using superconducting quantum interference device (SQUID) magnetometers for performing measurement of a magnetic field generated from the heart of an adult, child or foetus, and more particularly relates to a biomagnetic field measuring apparatus in which an ultrasonic transducer probe is arranged inside a shielded room, an ultrasonic tomographic image of a subject to be inspected and a waveform of a magnetic field generated from the heart of the inspected subject are displayed inside the shielded room, and the start of measurement of a biomagnetic field is controlled in the shielded room.

For diagnosis of heart disease of a foetus, ultrasonic examination has widely been used which can detect the shape and rough motion of the heart and the state of blood flow in the heart, but in the ultrasonic examination, cardiac activity of the heart muscle cannot be detected.

In the conventional biomagnetic field measurement, a waveform monitor unit is arranged outside a shielded room and an operator cannot confirm waveforms in the shielded room. Especially in the case of a magnetic field generated from the heart of foetus, the position of which is unstable, is desired to be detected, the operator must get information from a person who operates the monitor unit disposed outside the shielded room and determine a measuring location (Rev. Sci. Instrum. 66 (10), pp. 5085–5091 (1995)).

By measuring a magnetic field generated from the heart (hereinafter called a cardiac magnetic field) through the use of a biomagnetic field measuring apparatus, cardiac muscle activity can be diagnosed. On the other hand, with an ultrasonic diagnosis apparatus, the state of blood flow in the heart can be diagnosed.

In the conventional biomagnetic field measurement, much time is consumed to search a measuring location, raising a problem that magnetic field measurement at an optimum location is difficult to achieve. Further, a control unit for SQUID magnetometers and a unit for acquisition control of magnetic field waveforms are arranged outside the shielded room and therefore, there is a problem that a magnetic field waveform cannot be recorded within the most optimum time zone.

For the purpose of accurately diagnosing a heart disease, a result of measurement of a cardiac magnetic field and a result by the ultrasonic diagnosis apparatus which are obtained at substantially the same time must be correlated to each other to conduct diagnosis collectively. But when the conventional ultrasonic diagnosis apparatus using many magnetic materials is arranged in the shielded room, magnetic noise is generated and therefore the conventional ultrasonic diagnosis apparatus cannot be arranged inside the shielded room where the biomagnetic field measuring apparatus is arranged, thus raising a problem that an inspection based on the ultrasonic diagnosis apparatus cannot be carried out simultaneously with the measurement of the cardiac magnetic field.

In measurement of a very weak magnetic field generated from the heart of a foetus, it is necessary to approach a pickup coil of the biomagnetic field measuring apparatus to the heart of the foetus as closely as possible. But the foetus moves in the uterus and therefore, the position of the heart of the foetus is desired to be confirmed by means of the ultrasonic diagnosis apparatus, which can perform noninvasive diagnosis immediately before a magnetic field generated from the heart of the foetus is measured. Thus, the use of the ultrasonic diagnosis apparatus inside the shielded room has been desired strongly.

SUMMARY OF THE INVENTION

An object of the present invention is to provide a biomagnetic field measuring apparatus which can control, inside the shielded room, the start of observation of magnetic field waveforms measured from the heart of a subject to be inspected, magnetic field distribution and electric current distribution determined by computation and the measurement of the magnetic field waveforms and which can quickly position the sensors to optimum measuring locations.

Another object of the present invention is to provide an apparatus which can perform measurement of a biomagnetic field concurrently with ultrasonic inspection inside the shielded room.

A biomagnetic field measuring apparatus according to the present invention has, in a shielded room, a display for monitoring a magnetic field waveform generated from a heart of a foetus inside a subject to be inspected and magnetic field distribution and electric current distribution in the heart, a loudspeaker for generating a sound in synchronism with a heart beat of the heart, SQUID magnetometers, a switch for performing acquisition control of the magnetic field waveform, means for moving a bed, means for moving a gantry holding a cryostat, and an air mat for upward and downward motion of part of the inspected subject on the bed.

According to the biomagnetic field measuring apparatus according to the present invention, an operator inside the shielded room can observe, on a real time basis, magnetic field waveforms generated from the heart of the foetus inside the inspected subject in the form of a display picture on the display. As a result, the operator adapts SQUID magnetometers on the inspected subject so as to detect a maximum signal.

In the apparatus of the present invention, an ultrasonic transducer probe of the ultrasonic diagnosis apparatus is arranged inside the shielded room, a main body of the ultrasonic diagnosis apparatus including a transmitting circuit for transmission of an ultrasonic wave and a processor for receiving the ultrasonic wave and processing the received signal is arranged outside the shielded room, and an ultrasonic tomographic image is displayed on the display arranged inside the shielded room.

With the construction of the present invention which can permit confirmation of the results of measurement of the biomagnetic field and an ultrasonic tomographic image of the foetus in the inspected subject inside the shielded room, the operator inside the shielded room can observe the position of the heart of the foetus through the ultrasonic tomographic image on a substantially real time base when the magnetic field generated from the heart of the foetus is measured and consequently, the SQUID magnetometers can be positioned quickly to optimum measuring locations and the magnetic field generated from the heart of the foetus can be detected clearly with high sensitivity. When a magnetic field generated from an adult or a child is measured, the cardiac magnetic field can be measured while simultaneously observing a blood flow state in the heart through an ultrasonic tomographic image.

According to the biomagnetic field measuring apparatus according to the present invention, an abnormality of the heart of the foetus such as arrhythmia can be detected to permit early diagnosis of heart disease and important information about prenatal therapy and afterbirth therapy can be obtained.

As shown in FIGS. 1 and 7, the biomagnetic field measuring apparatus comprises a shielded room 1, a bed 4, SQUID magnetometers for detecting a magnetic field from a subject to be inspected, a cryostat 2 for maintaining the SQUID magnetometers at an extremely low temperature (liquid helium He temperature or liquid nitrogen temperature), gantry 180 for holding the cryostat, and a computer 90 for driving the SQUID magnetometers and acquiring outputs of driving detection circuit 50 for detecting signals from the SQUID magnetometers to perform computation. There are provided in the shielded room means (monitor display 80) for displaying one or more of a measured magnetic field waveform, measured electrocardiogram waveform, distribution of magnetic field obtained through computation and distribution of electric current obtained through computation, a SQUID magnetometer driving button 19a for controlling operation of the SQUID magnetometers, a data acquisition starting button 19b for controlling start of data acquisition and a loudspeaker 100 for generating beep sounds in synchronism with heart beats of a mother and a foetus, and there are provided outside the shielded room an amplifying and filtering unit 60 and means 11 for detecting a heart beat and a heart rate from measured magnetic field waveforms.

In order to detect a magnetic field generated from the heart of the foetus, the SQUID magnetometers for detection of, for example, 4 to 16 normal components (z components) of the magnetic field are arranged in a 2×2 to 4×4 matrix inside the cryostat 2. Distribution of magnetic field and distribution of electric current in the heart of the foetus can be obtained from magnetic field waveforms resulting from signals detected by the plurality of SQUID magnetometers. Further, when detailed information is needed, SQUID magnetometers for detecting three components (x, y and z components) of the magnetic field may be arranged in the matrix.

An ultrasonic transducer probe 8 is arranged inside the shielded room 1, and an ultrasonic diagnosis apparatus main body 6 including a transmitting circuit for transmitting an ultrasonic wave to a subject to be inspected and a processor for receiving a reflected ultrasonic wave from the inspected subject and processing the received signal is arranged outside the shielded room 1. An ultrasonic tomographic image signal-processed by the main body 6 is displayed on the monitor display 80. When constitutional elements of the main body 6 are formed by using non-magnetic materials and a magnetic field generated from the main body 6 is shielded enough not to interfere with detection of the magnetic field generated from the inspected subject, the main body 6 can be arranged internally of the shielded room at a position remote from the cryostat 2 incorporating the magnetometers.

DESCRIPTION OF THE PREFERRED EMBODIMENTS

Preferred embodiments of the present invention will now be described with reference to the accompanying drawings.

Figure 1:
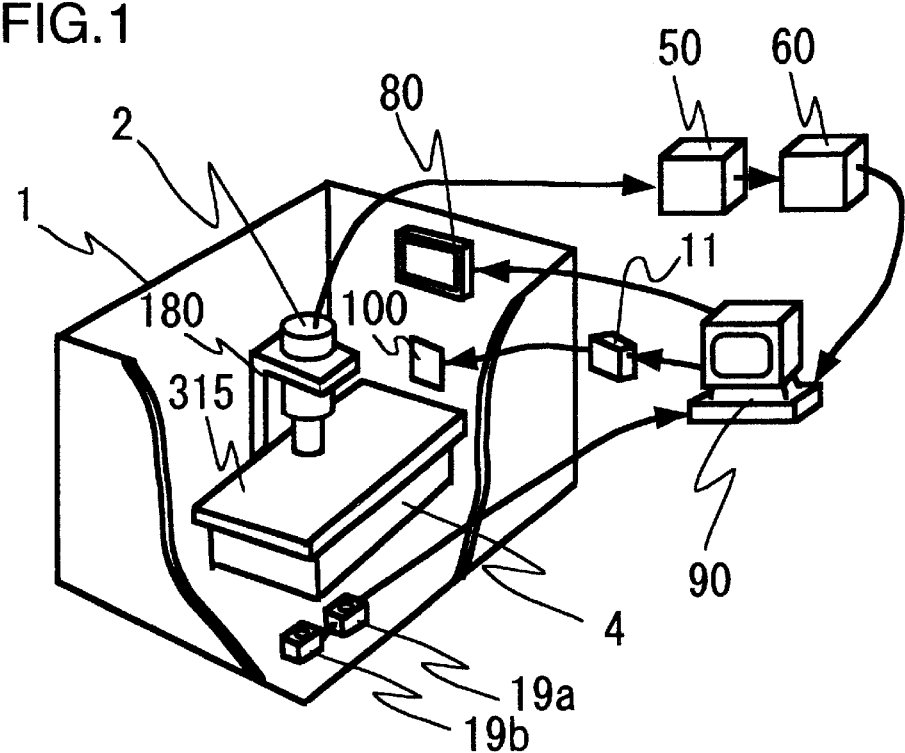
FIG. 1 is a diagram showing the construction of an embodiment of a biomagnetic field measuring apparatus according to the present invention.

Referring to FIG. 1, an embodiment of a biomagnetic field measuring apparatus according to the invention is constructed as shown therein. Arranged in a shielded room 1 as shown in FIG. 1 are a cryostat 2 for maintaining SQUID magnetometers at an extremely low temperature, a gantry 180 for holding the cryostat 2, a bed 4 on which a subject to be inspected lies, a SQUID magnetometer driving button 19a which controls the operation of the SQUID magnetometers, a data acquisition starting button 19b for controlling the start of data acquisition, a monitor display 80 for displaying output waveforms of the SQUID magnetometers and a loudspeaker 100 for generating beep sounds in synchronism with beats of hearts (heart beats) of a mother and a foetus. In order to avoid generation of magnetic field noise, the SQUID magnetometer driving button 19a and the data acquisition starting button 19b are positioned remotely from the SQUID magnetometers. Preferably, each of the buttons 19a and 19b may be, for example, an infrared-ray operable switch which generates less current. Preferably, the monitor display 80 may be a monitor unit which generates less of a magnetic field such as a liquid crystal display, plasma display or projecting display.

Arranged externally of the shielded room are a driving and detection circuit 50 for driving the SQUID magnetometers to detect magnetic signals therefrom, an amplifying and filtering unit 60 for amplifying or filtering outputs of the driving and detection circuit 50, a computer 90 for collecting, as digital data, outputs of the amplifying and filtering unit 60 and a heart rate detection unit 11 for detecting heart beat and heart rate of a heart from a measured magnetic field. The heart rate detection unit 11 is constructed to have, for example, a circuit which applies bandpass filtering of a narrow band (10 Hz to 20 Hz) to a magnetic signal generated from the heart to perform peak detection. But, a similar heart rate detection may be carried out by using software.

Figure 2:
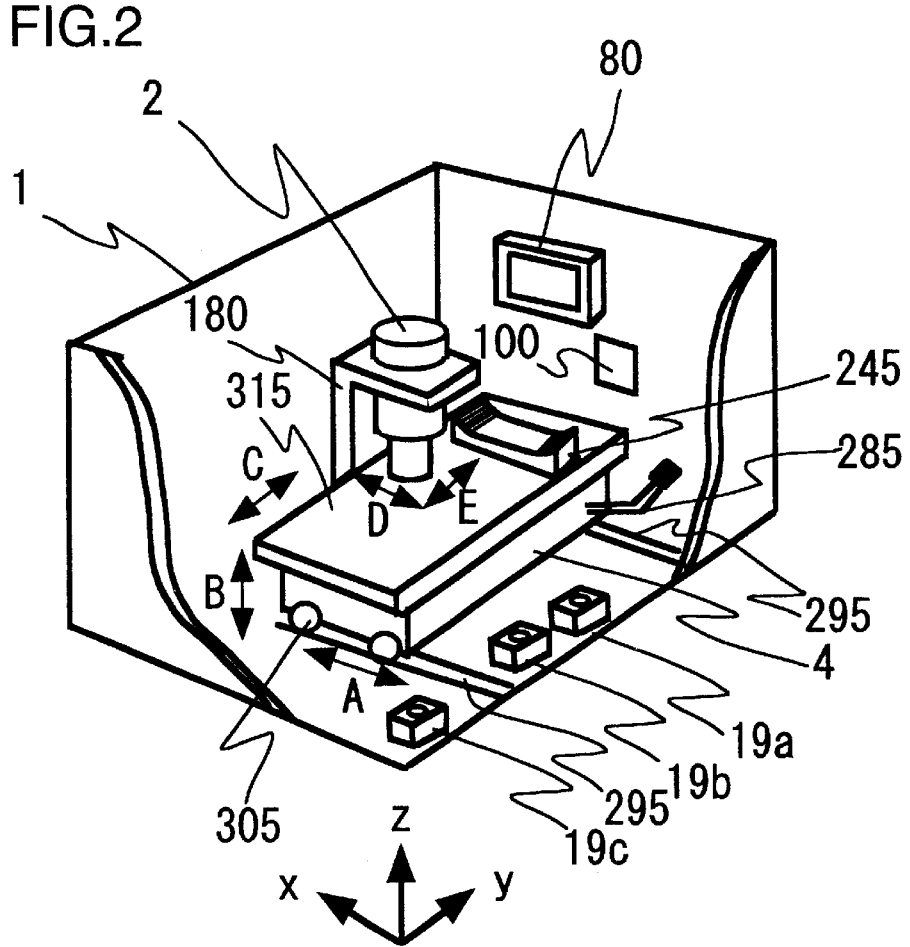
FIG. 2 is a diagram showing details of the construction of part of the biomagnetic field measuring apparatus inside a shielded room an embodiment of the present invention.

The construction of part of the biomagnetic field measuring apparatus of the present embodiment inside the shielded room is detailed in FIG. 2. By rotating four wheels 305 attached to the bottom of the bed along rails 295 laid on the floor of the shielded room, the whole of the bed can be moved in the A direction (bed minor axis direction). Movement of the bed in the B direction (upward or downward direction) can be adjusted finely by means of an up/down movement lever 285 interlocked with an oil-pressure cylinder. Movement of the bed in the C direction (bed major axis direction) can be adjusted finely by sliding a top plate of bed 315. The gantry 180 holding the cryostat 2 can rotate the cryostat 2 in the D direction (in the xz plane) and in the E direction (in the yz plane). Further, arranged on the bed is an air mat 245 which raises a part of the body of the subject to be inspected to cause the heart (the heart of a grownup or a foetus) to approach a lower end of the cryostat 2. The movements of the bed in the A, B and C directions, the movements of the gantry 180 in D and E directions and the up/down movement of the air mat 245 can be controlled either manually or by means of a remote control lever 19c.

The procedure of measurement of a biomagnetic field in the apparatus shown in FIGS. 1 and 2 will be described below. When a subject to be inspected lies on the bed 4, an operator in the shielded room 1 moves the bed 4 in the up/down direction, right and left direction and to-and-fro direction (B, C and A directions) manually or by means of the remote control lever 19c to position the cryostat 2 incorporating the SQUID magnetometers to the heart of the patient. The gantry 180 is rotated in the D and E directions as necessary to keep an optimum positional relation between the heart of the inspected subject and the cryostat 2. At the time that the distance between the heart of the inspected subject and the cryostat 2 approaches about 20 cm, the operator depresses the SQUID magnetometer driving button 19a to drive the SQUID magnetometers. While watching output waveforms from the SQUID magnetometers on the monitor display 80 and at the same time listening to a beep sound which is generated from the speaker 100 concomitantly with a heart beat of the heart of the inspected subject, the operator makes a final fine adjustment. After completion of the fine adjustment, the operator depresses the data acquisition starting button 19b at the time that a magnetic field waveform is desired to be recorded while watching magnetic field waveforms on the monitor display 80, thereby causing the desired magnetic field waveform to be collected into the computer 90. The above is the general operational procedure.

Figure 3:
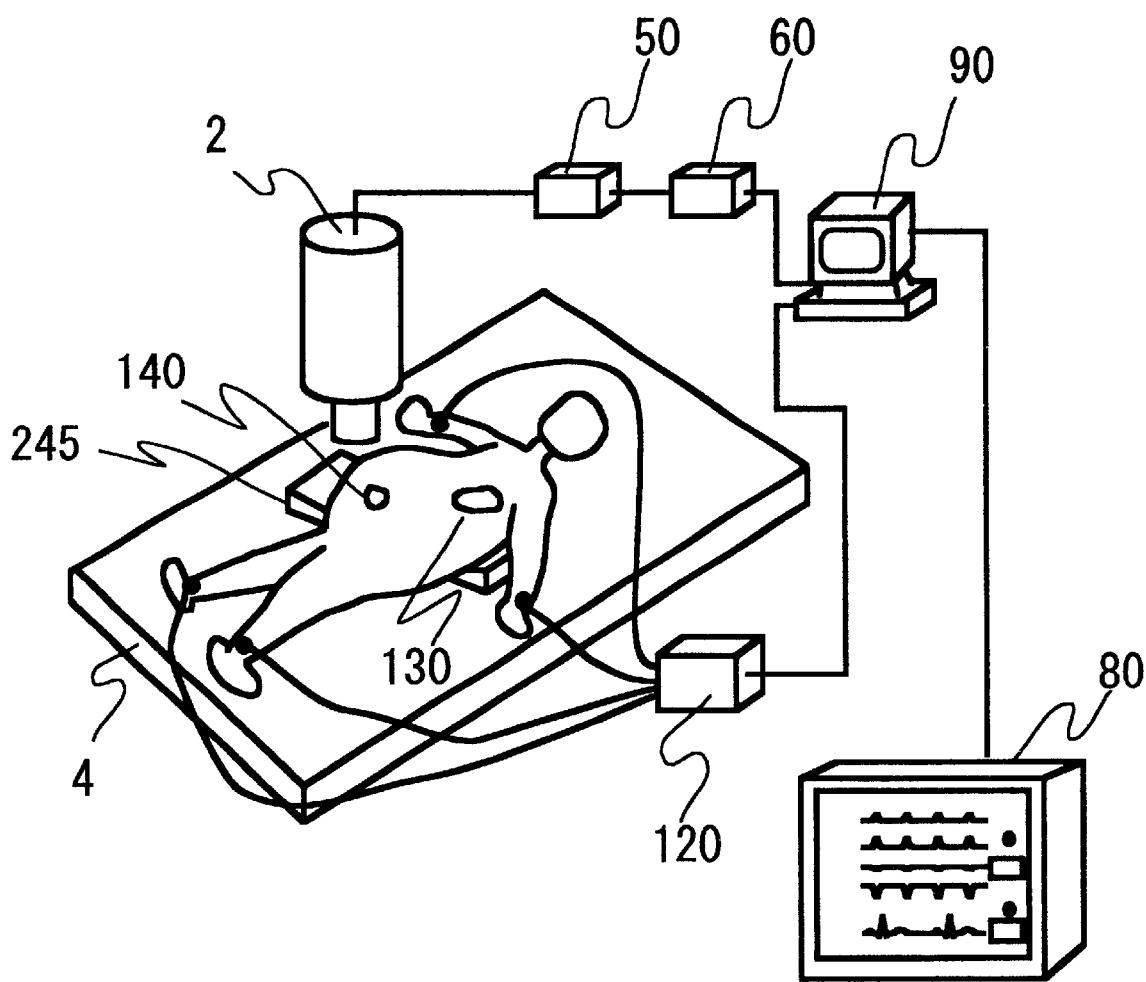
FIG. 3 is a diagram showing the construction for measurement of a magnetic field generated from a heart of a foetus an embodiment of the present invention.

Referring now to FIG. 3, an embodiment of magnetic field measurement for detecting a magnetic field generated from a heart of a foetus according to the invention will be described. In order to distinguish a magnetic field generated from a heart 130 of a mother from that generated from a heart 140 of the foetus, and electrocardiogram measurement of the mother is carried out by means of a bipolar standard lead electrocardiograph 120 simultaneously with magnetic field measurement based on the SQUID magnetometers inside the cryostat 2. Electrocardiogram information of the mother and magnetocardiogram information of the foetus obtained by means of the SQUID magnetometers inside the cryostat 2 are displayed at a time on the monitor display 80. While watching magnetic field waveforms of the heart of the foetus and listening to a beep sound due to a heart beat of the heart of the foetus, the operator can search the location of the heart of the foetus by moving either the bed 4 or the cryostat 2. In this manner, an optimum position for detection of a magnetic field of the heart of the foetus can be selected while bringing the bottom of the cryostat 2 into intimate contact with the belly surface of the mother (see FIG. 11). As a filter constituting the amplifying and filtering unit 60, an analog filter or a digital filter is used which can block a frequency component of 2 to 3 Hz in the output signal of the driving and detection circuit 50 and can pass a signal having a predetermined frequency band (4 to 5 Hz or more) with the aim of eliminating noise caused by motion of the belly of the mother due to breathing (motion of the belly at 2 to 3 Hz applies a vibration to the cryostat and this vibration is transmitted to the SQUID magnetometers, giving rise to generation of noise).

Figure 4:
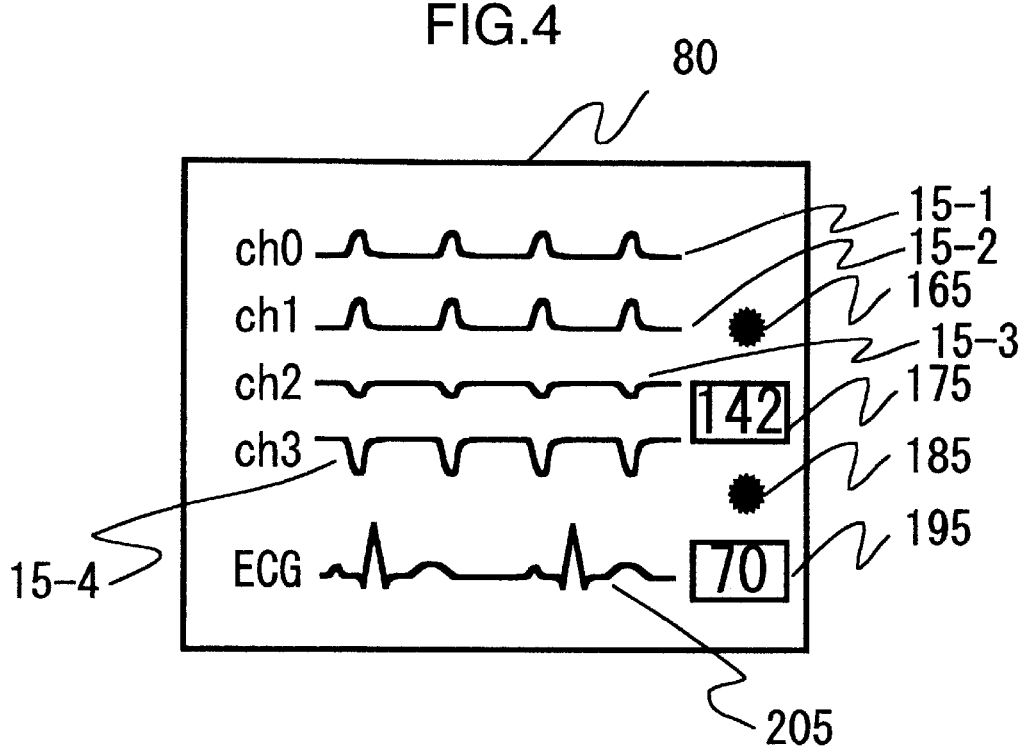
FIG. 4 is a diagram showing an example of a picture illustrative of the results of measurement of a magnetic field generated from the heart of foetus an embodiment of the present invention.

FIG. 4 shows an example of a picture indicating results of measurement of the magnetic field generated from the heart of foetus, that is, a picture displayed on the monitor display 80 during detection of the magnetic field generated from the heart of the foetus shown in FIG. 3. As shown at the upper part of the screen, a magnetic field which is generated from the heart of the foetus and detected at channels 0, 1, 2 and 3 of the SQUID magnetometers is on a real time basis from left to right of the screen to display magnetic field waveforms 15-1, 15-2, 15-3 and 15-4. Concurrently therewith, an electrocardiogram (ECG) 205 of the mother is swept so as to be displayed as shown at lower part of the screen. The operator confirms that the magnetic field generated from the heart of the foetus is detected by knowing that peak positions of the waveforms 15-1, 15-2, 15-3 and 15-4 at the upper part do not coincide with peak positions of the waveform 205 at the lower part.

The picture contains a region 175 for displaying a heart rate of the heart of the foetus represented by a numerical value indicative of the heart rate detected from the waveforms 15-1, 15-2, 15-3 and 15-4 (heart rate=142 in FIGS. 4 and 5), a flashing indicator 165 synchronized with the heart beat of the foetus which flashes in synchronism with a heart beat of the foetus in order to inform the timing of the heart beat of the foetus, a region 195 for displaying a heart rate of the heart of the mother represented by a numerical value indicative of the heart rate of the mother obtained from the electrocardiogram 205 of the mother at the lower part (heart rate=70 in FIGS. 4 and 5), and a flashing indicator 185 synchronized with the heart beat of mother which flashes in synchronism with a heart beat of the mother in order to inform the timing of the heart beat of the heart 130 of the mother. Alternatively, the heart rate of the mother may be extracted from the bipolar standard lead electrocardiograph 120 or magnetic field waveforms generated from the heart 130 of the mother.

Concurrently with flashing of the flashing indicator 165 synchronized with the heart beat of the foetus, which informs the timing of the heart beat of the foetus, a beep sound conforming to the heart beat of the foetus is generated from the loudspeaker 100.

As necessary, a beep sound corresponding to the heart beat of the heart 130 of the mother may also be generated concurrently. While consulting the beep sound synchronized with the heart beat of the foetus generated from the loudspeaker 100, the flashing indicator 165 synchronized with the heart beat of the foetus and the magnetic field waveforms 15-1 to 15-4 generated from the heart of the fetus, the operator can rapidly position the cryostat 2 incorporating the SQUID magnetometers to an optimum location on the belly of the pregnant woman where the magnetic field signals generated from the heart of the foetus can be detected.

Figure 5:
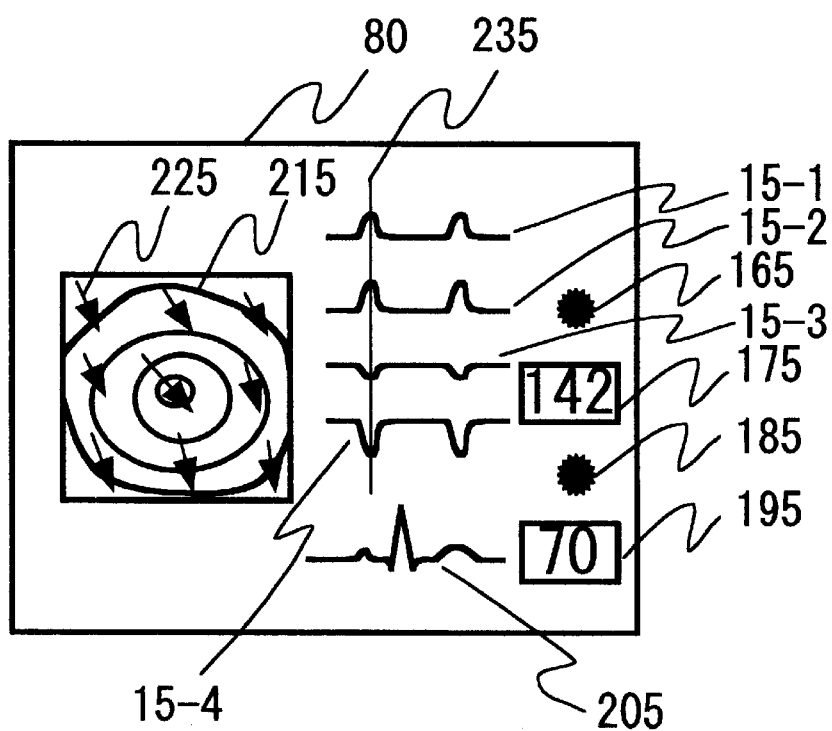
FIG. 5 is a diagram showing another example of a picture illustrative of the results of measurement of a magnetic field generated from the heart of the foetus an embodiment of the present invention.

FIG. 5 shows another example of a picture indicating results of measurement of the magnetic field generated from the heart of the foetus, that is, a picture displayed on the monitor display 80 during detection of the magnetic field generated from the heart of the foetus shown in FIG. 3. A distribution map of magnetic field 215 at the heart of the foetus and a distribution map 225 of electric current at the heart of the fetus are displayed on the monitor display 80 on a real time basis, along with a waveform display of magnetic field waveforms 15-1, 15-2, 15-3 and 15-4 generated from the heart of the foetus and a waveform display of an electrocardiogram 205 of the mother.

The distribution map of magnetic field 215 is displayed by using any of a distribution of magnetic field components ($B_z$ components) in normal direction measured by a plurality of SQUID magnetometers, an absolute value ($\sqrt{(B_x^2 + B_y^2)}$) of each set of measured magnetic field components ($B_x$, $B_y$) in the tangential direction and an absolute value ($\sqrt{(dB_z/dx)^2 + (dB_z/dy)^2}$) of differential values ($dB_z/dx$, $dB_z/dy$) of each measured magnetic component in the normal direction.

The distribution map of magnetic field 215 shown in the example of FIG. 5 is obtained from the absolute value ($\sqrt{(dB_z/dx)^2 + (dB_z/dy)^2}$) of differential values ($dB_z/dx$, $dB_z/dy$) of a magnetic field component in the normal direction ($B_z$ component) measured by nine SQUID magnetometers.

The distribution map of electric current 225 indicates a direction which results from a 90° counterclockwise rotation of a vector value of the measured magnetic components ($B_x$, $B_y$) in the tangential direction or a direction which results from a 90° counterclockwise rotation of a vector value of the differential values ($dB_z/dx$, $dB_z/dy$) of the measured magnetic field component in the normal direction.

Like the picture of FIG. 4, the picture of FIG. 5 contains a flashing indicator 165 synchronized with the heart beat of the foetus, a region 175 for displaying a heart rate of the foetus, a flashing indicator 185 synchronized with the heart beat of the mother, and a region 195 for displaying a heart rate (heart rate=70 in FIGS. 4 and 5) of the mother.

When peak values of magnetic field signals generated from the heart of the foetus are detected by the detection unit for heart rate 11, the displayed magnetic field distribution map and electric current distribution map are obtained at a time phase indicated by a line 235. Each of the magnetic field distribution map 215 and the electric current distribution map 225 may be displayed at all heart beats or once every 2 to 3 heart beats. While watching the magnetic field distribution map 215 or electric current distribution map 225 and magnetic field waveforms 15-1 to 15-4 generated from the heart of the foetus, the operator can move the bed 4 or the gantry 180 to determine either a location where the magnetic field generated from the heart of the foetus is the most intensive or an observation range.

By making the vertical direction of the magnetic field distribution map 215 or the electric current distribution map 225 displayed on the screen coincident with sensor positions determined when the operator views the mother from the side of cryostat 2 above the bed 4, it can be decided which portion of the mother is intensively affected by the magnetic field generated from the heart of the the foetus and therefore, the position of the foetus in the mother can be known with ease.

Figure 6:
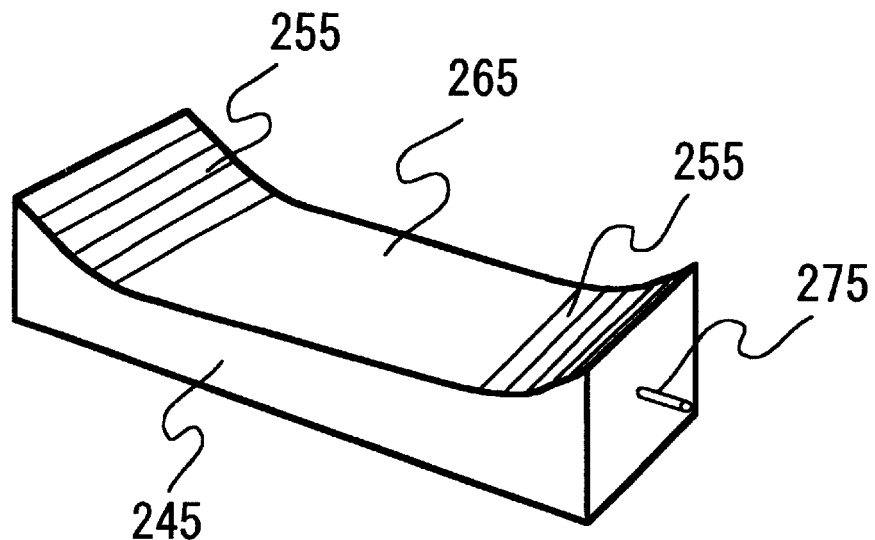
FIG. 6 is a perspective view of an air mat in the embodiment of the present invention.

The air mat 245 disposed between the vicinity of the lower abdomen of the pregnant woman where the heart 140 of the foetus shown in FIG. 3 lies and the bed 4 is constructed as shown in FIG. 6. The air mat shown in FIG. 6 takes a state when air is filled maximally into the air mat 245 through an air inlet port 275. To prevent the pregnant woman from rolling over and falling down from the air mat 245, the air mat has roll-over preventive guides 255 on both sides of a flat part 265. The pregnant woman lies face up or lies side down so that the lower abdomen may be positioned on the withered air mat 245.

Thereafter, the operator injects air into the air mat 245 through the air inlet port 275 by means of a pump or the like to raise the lower abdomen of the pregnant woman. Since the cryostat 2 can be kept away from the heart 130 of the pregnant woman by raising only the lower abdomen of the pregnant woman, separation of only magnetic signals generated from the heart of the foetus can be facilitated. The supply of air to the air mat 245 can also be adjusted by the remote control lever 19c.

Figure 7:
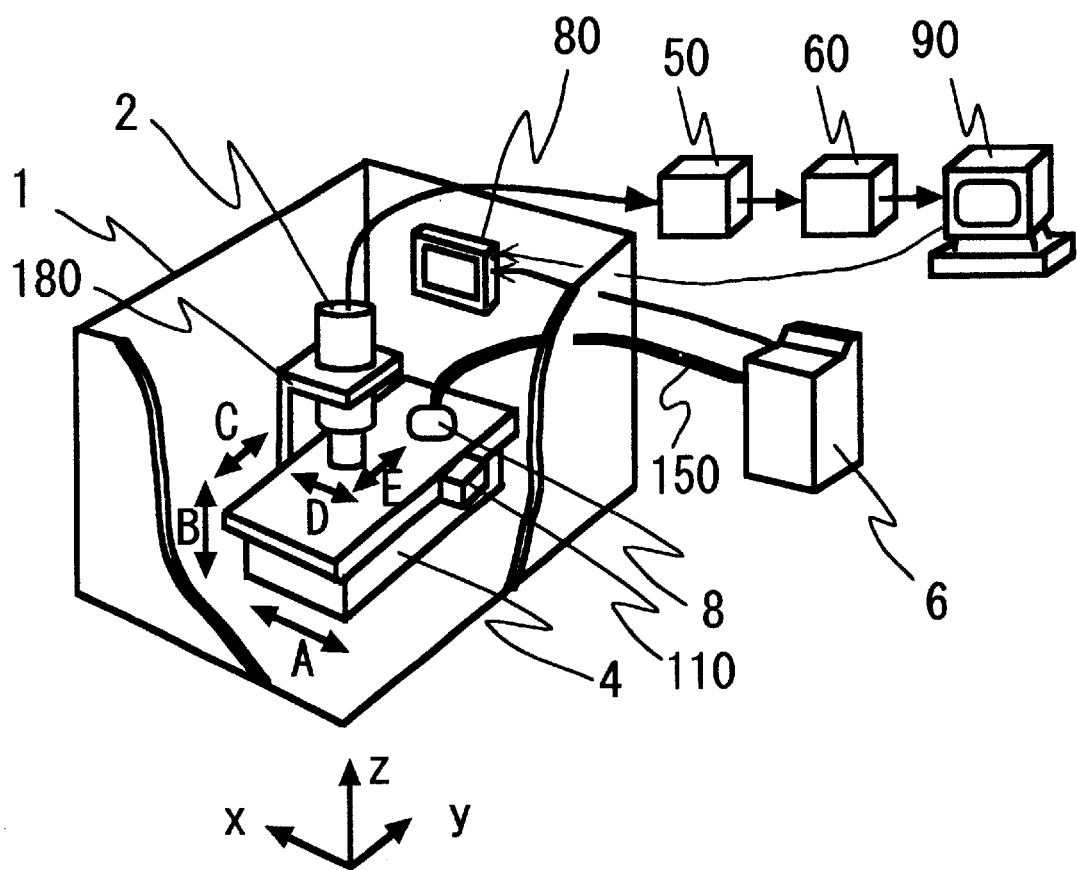
FIG. 7 is a diagram showing the construction of another embodiment of the biomagnetic field measuring apparatus according to the invention.

Another embodiment of the biomagnetic field measuring apparatus according to the present invention is constructed as shown in FIG. 7. As compared to the apparatus constructed as shown in FIG. 1, an ultrasonic tomographic image can additionally be observed in the shielded room according to the present embodiment. In describing the construction in connection with FIG. 7, components common to FIG. 1 will not be described. As shown in FIG. 7, arranged in the shielded room 1 are an ultrasonic transducer probe 8 for performing ultrasonic inspection of an inspected subject (not shown) lying on the bed 4, a monitor display 80 for displaying an ultrasonic tomographic image obtained by signal-processing a reflected ultrasonic wave generated from the inspected subject and received by the ultrasonic transducer probe 8, and a controller 110 for setting gain and focus of an ultrasonic diagnosis apparatus and various kinds of photographing modes (measurement modes). Used as various kinds of photographing modes are A mode, B mode, M mode and Doppler mode or CFM mode as will be described later.

Arranged externally of the shielded room 1 is a main body 6 of the ultrasonic diagnosis apparatus incorporating a measuring circuit of the ultrasonic diagnosis apparatus (including a transmitting circuit for transmission of an ultrasonic wave and a processor for receiving the ultrasonic wave and processing the received signal). The main body 6 of the ultrasonic diagnosis apparatus is connected to the ultrasonic transducer probe 8, monitor display 80 and controller 110 which are arranged internally of the shielded room 1, thus establishing the overall construction of the ultrasonic diagnosis apparatus.

Next, an example of the procedure for measuring a weak magnetic field generated from a heart of a foetus with the apparatus of the present invention will be described. Although not described in connection with FIG. 1, the bed 4 is movable along its minor axis (in the A direction or x direction), along its major axis (in the C direction or y direction) and along its vertical direction (B direction or z direction) and the cryostat 2 can be rotated in the D direction (in the xz plane) and E direction (in the yz plane) by means of the gantry 180. A subject to be inspected lies on the bed 4 which is drawn out in the A direction (x direction) from a position beneath the cryostat 2. While contacting the ultrasonic transducer probe 8 with the belly of the inspected subject and watching an ultrasonic image (for example, a B mode image), the operator confirms the position of the heart of the foetus, brings the bottom of cryostat 2 to a position as close to the confirmed position as possible, adjusts the moving amounts of the bed 4 in the A, B and C directions and the tilt amounts of the gantry 180 in the D and E directions to position the cryostat 2 to an optimum location, and executes measurement of the cardiac magnetic field of the foetus.

Figure 8:
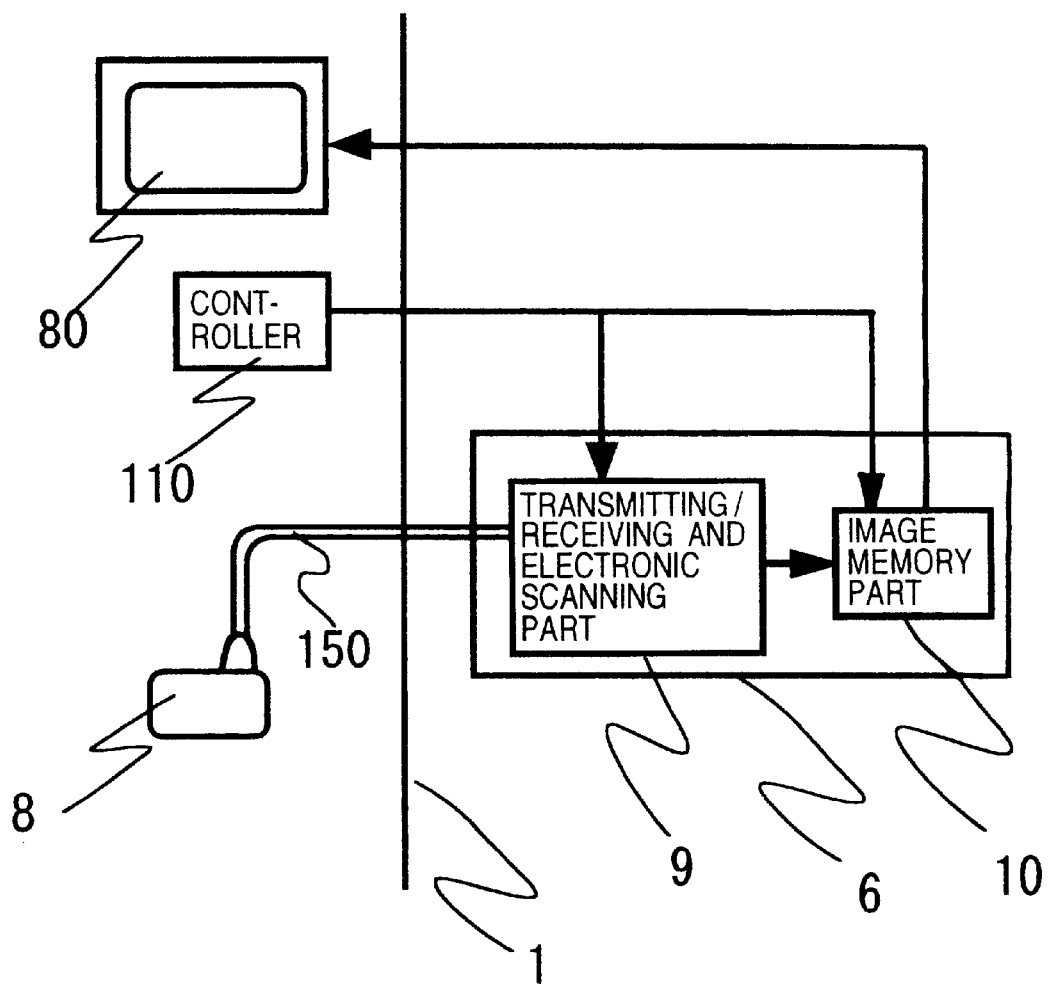
FIG. 8 is a diagram showing the overall construction of an ultrasonic diagnosis apparatus used in the biomagnetic field measuring apparatus an embodiment of the present invention.

Referring to FIG. 8, there is illustrated the construction of the whole of the ultrasonic diagnosis apparatus used in the biomagnetic field measuring apparatus of a preferred embodiment of the present invention. Arranged in the shielded room 1 are the ultrasonic transducer probe 8, controller 110 and monitor display 80. The ultrasonic transducer probe 8 is connected to a transmitting/receiving and electronic scanning part 9 of the ultrasonic diagnosis apparatus main body 6 which is arranged externally of the shielded room 1 through a cable 150 such as a coaxial flat cable. An echo signal obtained from the transmitting/receiving part and electronic scanning part 9 is signal-processed by a signal processor (not shown) to provide image data which in turn is stored in an image memory part 10 and displayed, as an ultrasonic image, on the monitor display 80 arranged internally of the shielded room 1. As in the construction of FIG. 1, measured magnetic waveforms and the like are also delivered to the monitor display 80.

Figure 9:
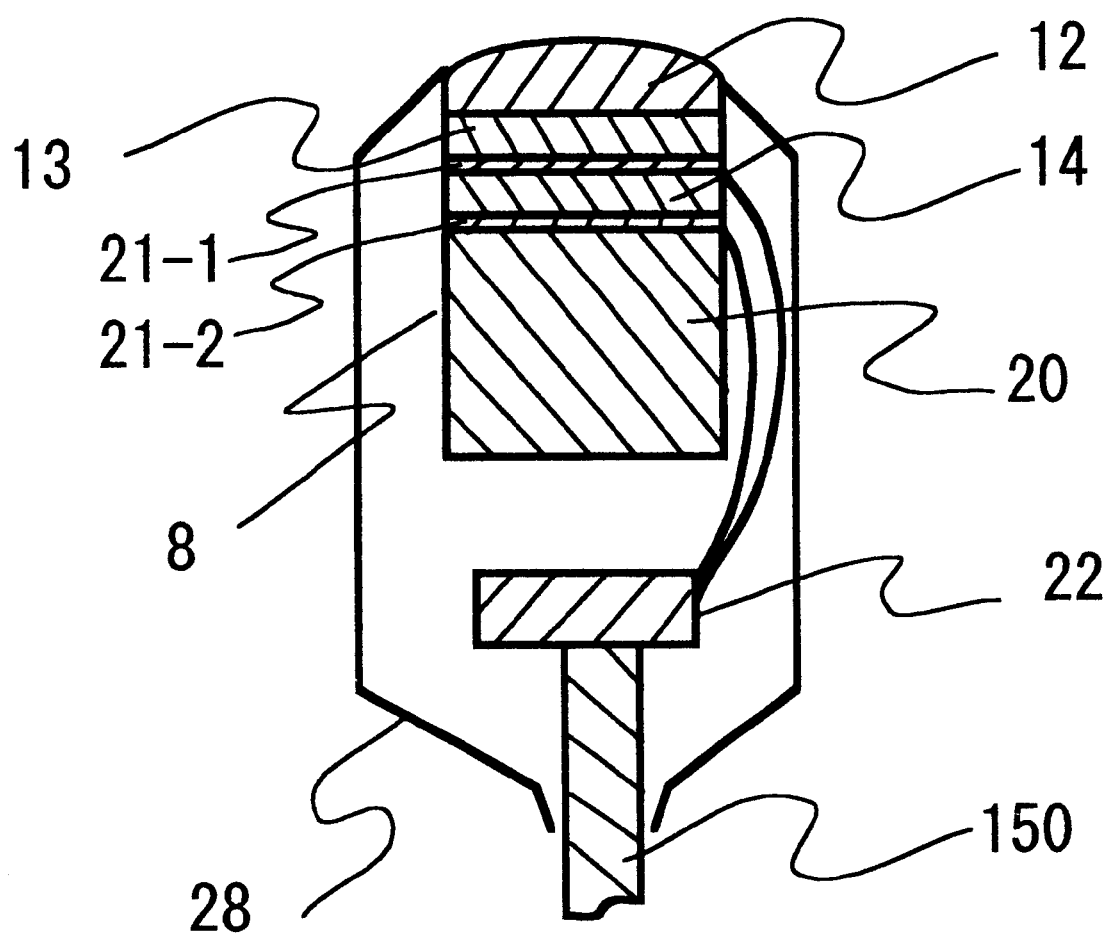
FIG. 9 is a sectional view showing the construction of an ultrasonic transducer probe used an embodiment of the present invention.

The ultrasonic transducer probe 8 used in this embodiment of the present invention is constructed as shown in FIG. 9. Used for piezoelectric ceramics (transducer) 14 constituting the ultrasonic transducer is a piezoelectric material which has a piezoelectric characteristic obtained by polarizing ceramics such as lead titanate zirconate or lead titanate under a high electric field, or a piezoelectric polymer material such as polyvinylidene fluoride (PVDF). Especially when the ultrasonic transducer probe is used near the SQUID magnetometers, the use of PVDF which is a non-magnetic material is preferable. The piezoelectric ceramics 14 has first and second surfaces on which a signal electrode 21-1 and a high voltage electrode 21-2 are formed, respectively, and an acoustic matching layer 13 for acoustic matching with the living body is formed on the signal electrode 21-1. The acoustic matching layer 13 is formed by mixing epoxy resin or fused silica with a filler of various kinds of non-magnetic materials and is set to have an optimum acoustic impedance.

For example, when acoustic matching is effected with one layer, this layer has an impedance of $\sqrt{(Z_M Z_0)}$ and a thickness of $\lambda/4$ as is well known in the art, where $\lambda$ is the wavelength of an ultrasonic wave, $Z_M$ is the acoustic impedance of a medium (here, a living body) and $Z_0$ is a acoustic impedance of the piezoelectric ceramics. Arranged on the acoustic matching layer 13 is an acoustic lens 12 which forms an emitted ultrasonic wave into a focusing beam.

For example, an acoustic lens 12 is used in which sound speed, acoustic impedance and acoustic wave attenuation are set to optimum values by mixing silicon rubber with a filler of non-magnetic material such as $SiO_2$. In the acoustic lens, the sound speed is about 1500 m/sec, the acoustic impedance is about 1.5 M Rayls and the acoustic wave attenuation is preferred to be as small as possible. Arranged on the back of the piezoelectric ceramics 14 is a backing material 20 which plays the role of mechanically supporting the piezoelectric ceramics 14 (transducer) and of acoustically damping the ultrasound pulse waveform to shorten it. The backing material 20 is formed by press forming epoxy resin mixed with a powder of a non-magnetic material such as tungsten oxide or titanium oxide. The signal electrode 21-1 and high voltage electrode 21-2 are electrically connected to the transmitting/receiving part and electronic scanning part 9 of the ultrasonic diagnosis apparatus main body 6 by a cable 150 such as a coaxial flat cable through a connector 22.

Most of the acoustic lens 12, the acoustic matching layer 13, the electrodes 21-1 and 21-2, the piezoelectric ceramics 14, the backing material 20, the connector 22 and the cable 150 are housed in a case 28. Preferably, plastics is used as a material of the case 28 and when the application of an electromagnetic shield is needed, the case 28 is electromagnetically shielded by a non-magnetic material such as aluminum or copper.

Figure 10:
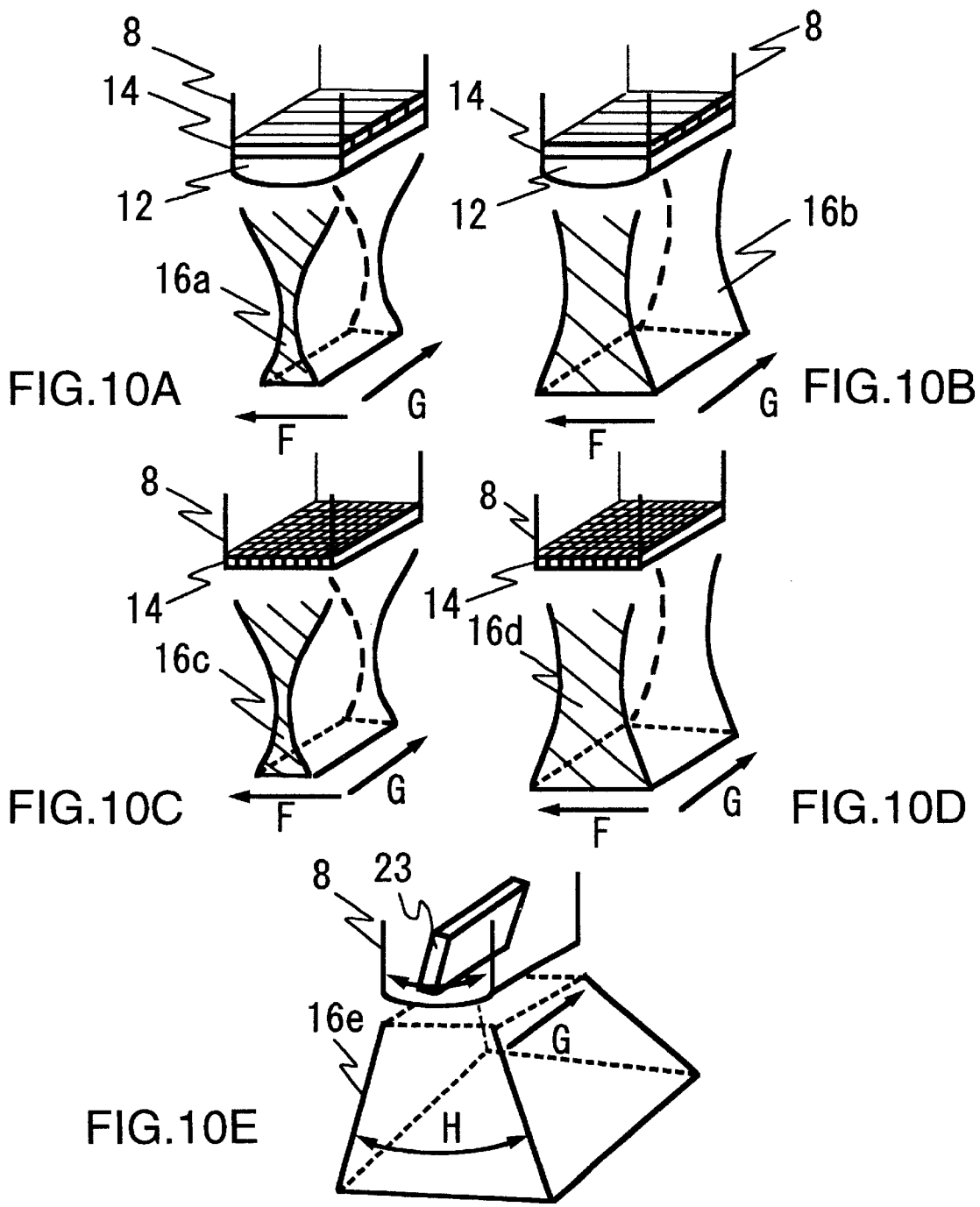
FIGS. 10A, 10B, 10C, 10D and 10E are diagrams showing examples of the range of view field in the slice direction of the ultrasonic transducer probe comprised of an array transducer used an embodiment of the present invention.

Examples of the range of view field in the slice direction (indicated by F) of the ultrasonic transducer array probe used inside the shielded room in the embodiment of the present invention are shown in FIGS. 10A, 10B, 10C, 10D and 10E. In FIGS. 10A and 10B, ranges of view field 16a and 16b obtained when a linear array probe (one-dimensional array transducer) is used are shown, with G indicating electron scanning direction and F indicating slice direction. FIG. 10A shows the range of view field 16a when ultrasonic waves generated from the ultrasonic transducer array (piezoelectric ceramics) 14 are narrowly focused by means of the acoustic lens 12, and FIG. 10B shows the range of view field 16b which is obtained when ultrasonic waves generated from the ultrasonic transducer array (piezoelectric ceramics) 14 are broadly focused by means of the acoustic lens 12 in order that the body surface of the foetus is integrated in the slice direction (indicated by F) to provide a three-dimensional ultrasonic image.

FIGS. 10C and 10D show the ranges of view field 16c and 16d, respectively, obtained when the piezoelectric ceramics is divided also in the slice direction (indicated by F) in order that a probe (two-dimensional array transducer) can be utilized which focuses ultrasonic waves under electron scanning not only in the electron scanning direction (indicated by G) but also in the slice direction in the same way. FIG. 10C shows the range of view field 16C obtained when ultrasonic waves are narrowly focused under electron scanning. In FIG. 10D, ultrasonic waves are broadly focused under electron scanning in the two directions to ensure that a three-dimensional ultrasonic image of the body surface of the foetus can be obtained. In FIG. 10E, by mechanically rotating a one-dimensional array transducer part 23 of linear array or convex array in a scanning direction orthogonal to the electron scanning direction in an acoustic coupling material inside the ultrasonic transducer probe 8, three-dimensional data which represents the range of view field 16e can be obtained, where H designates the rotation direction and G designates the electron scanning direction.

Through the ultrasonic wave scanning shown in FIG. 10E, a desired section display as well as a three-dimensional image of blood vessel unitizing color flow mapping (CFM) can be obtained. Preferably, the mechanical rotation motion is generated through a method which hardly generates a magnetic field such as a method using an ultrasonic motor. The three-dimensional scanning shown in FIG. 10E can be accomplished electronically by using the two-dimensional array transducer shown in FIGS. 10C and 10D.

Figure 11:
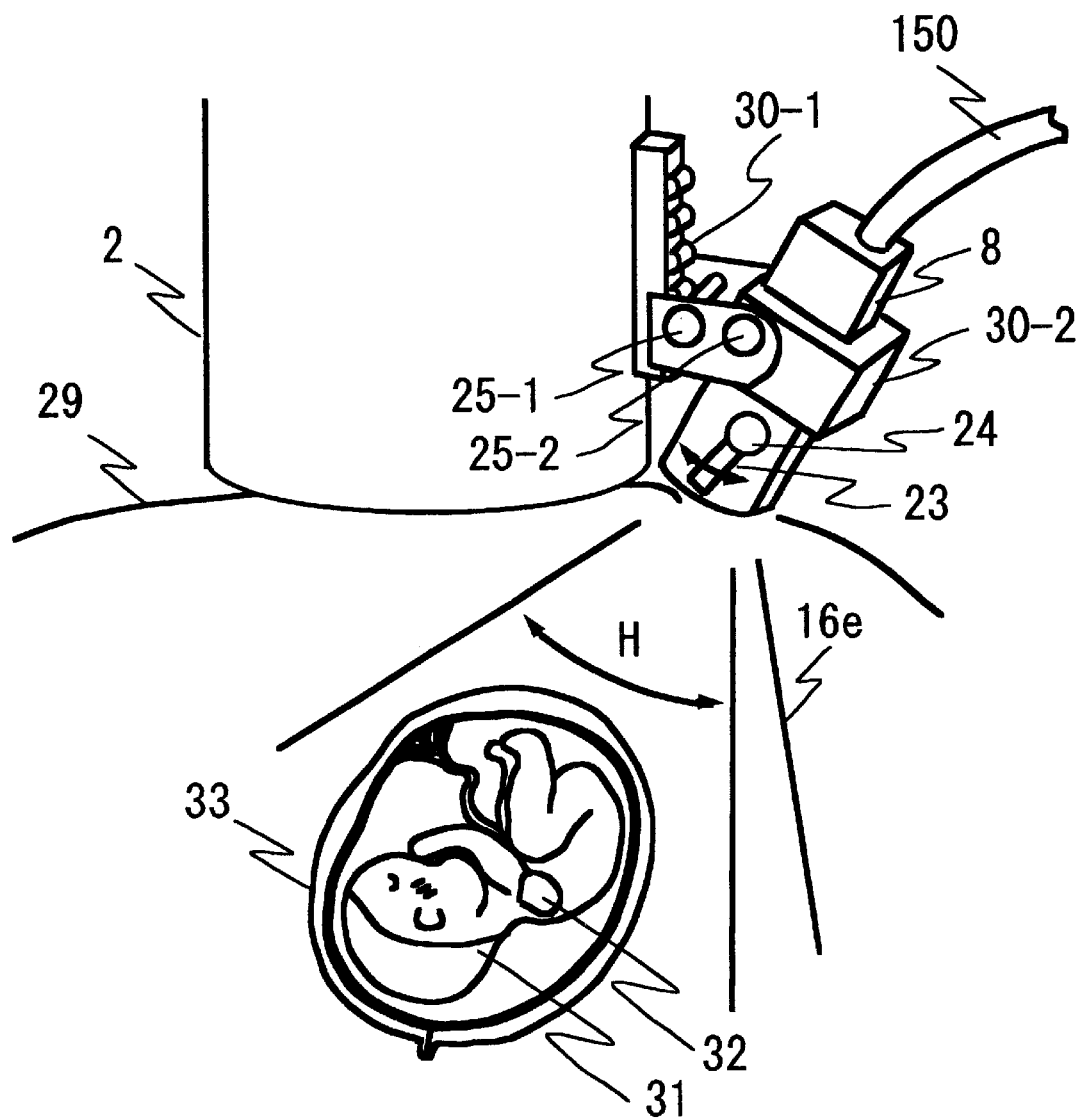
FIG. 11 is a perspective view for explaining the construction in which the ultrasonic transducer probe is mounted to a lower part of a cryostat an embodiment of the present invention.

The ultrasonic transducer probe comprised of the array transducer used inside the shielded room in the embodiment of the present invention and exemplified in FIGS. 10A, 10B, 10C, 10D and 10E can be mounted to a lower part of the cryostat 2. FIG. 11 is a diagram for explaining an embodiment in which the ultrasonic transducer probe for performing mechanical scanning shown in FIG. 10E is mounted to a lower part of the cryostat 2. The ultrasonic transducer probe 8 is mounted to a rack-pinion 30-1 fixed to the lower part of the cryostat 2 through the medium of a holder 30-2. By turning an upward/downward direction adjusting dial 25-1, the ultrasonic transducer probe 8 can be moved vertically along the side surface of the cryostat 2, and, by turning a dial 25-2, the angle of contact of the ultrasonic transducer probe 8 to the body surface can be changed to permit the fore end surface of the ultrasonic transducer probe 8 to make intimate contact with body surface 29.

As described previously, the one-dimensional array transducer part 23 is rotatable in the acoustic coupling material inside the ultrasonic transducer probe 8. The one-dimensional array transducer part 23 can be driven for rotation motion by the ultrasonic motor or the like but when noise caused during driving matters, the one dimensional array transducer 23 can be fixed to an optimum position for use through a manual operation based on a transducer direction setting dial 24. Consequently, as shown in, for example, FIG. 11, an ultrasonic tomographic image of a foetus 31 inside a uterus 33 of inspected subject 29 can be obtained in a specified orientation within the range of view field 16e, and in respect of the position of a heart 32 of the foetus 31, the position of the bottom of the cryostat for maintaining the SQUID's at a low temperature is adjusted such that a magnetic signal detected from the heart 32 of the foetus 31 can be maximized. The method set forth so far is effective especially for measurement of the magnetic field generated from the heart of the foetus in that simultaneously with measurement of a cardiac magnetic field of the foetus by means of the biomagnetic field measuring apparatus, motion of, for example, blood flow in the foetus can be monitored by means of the ultrasonic diagnosis apparatus.

When magnetic fields generated from hearts of foetuses of twins are desired to be measured, the position of the heart of each twin foetus is confirmed by using the ultrasonic transducer probe 8 explained previously and the bottom of the cryostat is approached to the heart of each foetus to permit separate measurement of a magnetic signal generated from the heart of each foetus. In the foregoing description, the ultrasonic transducer probe shown in FIG. 10E for performing mechanical scanning is exemplarily described as being mounted to the lower part of the cryostat 2, but the ultrasonic transducer probe as shown in FIGS. 10A, 10B, 10C, 10D or 10E, comprised of the one-dimensional or two-dimensional array transducer used in the shielded room, can also be mounted to the lower part of the cryostat 2.

Figure 12:
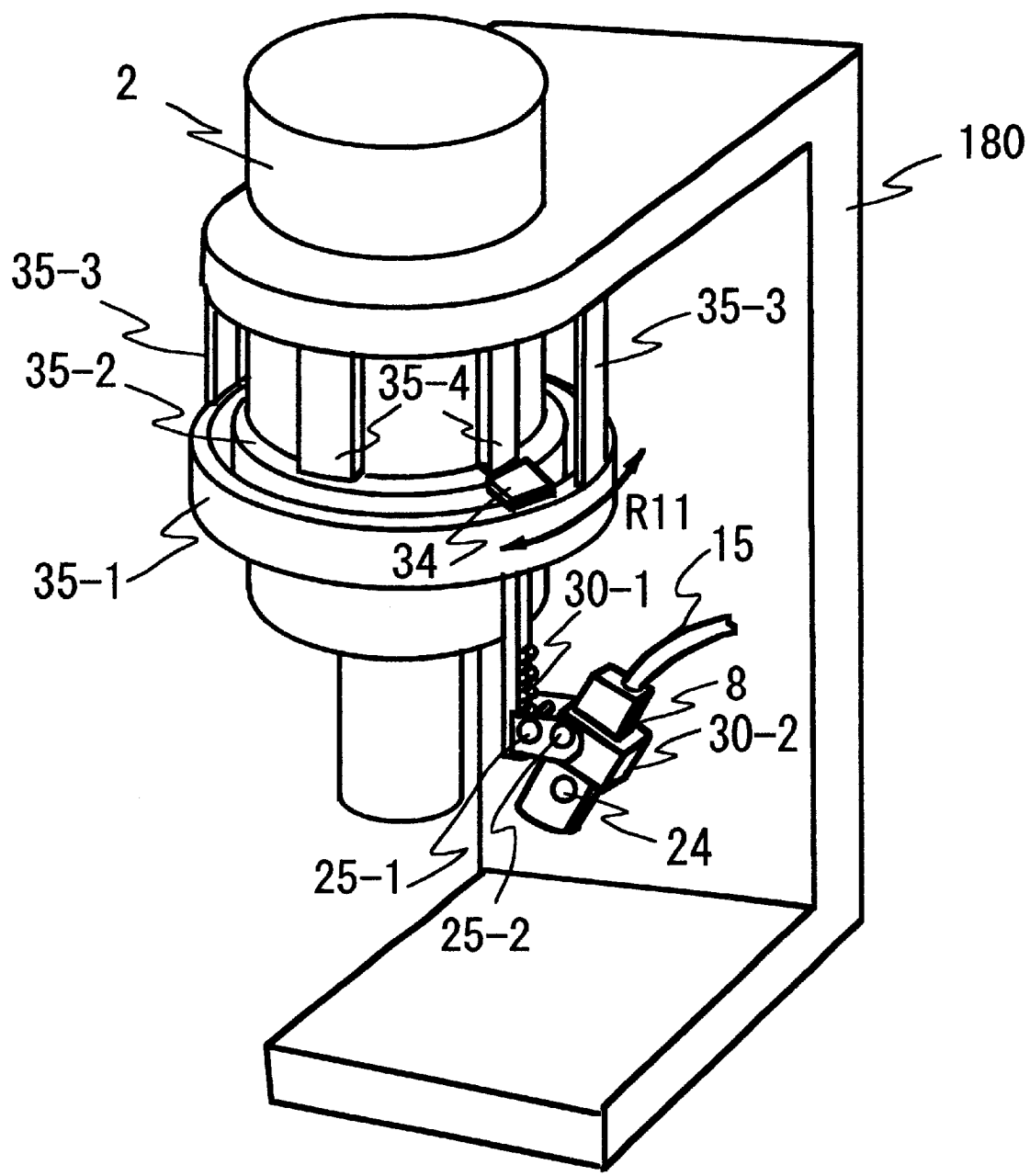
FIG. 12 is a perspective view for explaining the construction in which the ultrasonic transducer probe is mounted to a part of a gantry an embodiment of the present invention.

In the embodiment of the present invention, the ultrasonic transducer probe as shown in FIGS. 10A, 10B, 10C, 10D or 10E, comprised of the array transducer used in the shielded room, can be provided to part of the gantry 180 holding the cryostat 2. FIG. 12 is a diagram for explaining an embodiment in which the ultrasonic transducer probe shown in FIG. 10E for performing mechanical scanning is mounted to a part of the gantry 180. The cryostat 2 is circumferentially surrounded (in the R11 direction) by an inner guide rail 35-2 which in turn is held by the gantry 180 through the medium of inner holding members 35-4.

Further, on the outside of the inner guide rail 35-2, an outer guide rail 35-1 is held by the gantry 180 through the medium of outer holding members 35-3. A rack-pinion 30-1 is rotatable in the circumferential direction is (R11 direction) of the cryostat 2 between the outer guide rail 35-1 and the inner guide rail 35-2.

A stopper 34 for fixing the rotational position of the rack-pinion 30-1 between the outer guide rail 35-1 and the inner guide rail 35-2 is provided at the top end of the rack-pinion 30-1. The ultrasonic transducer probe 8 for performing mechanical scanning is provided to the bottom end of the rack-pinion 30-1 so as to be positioned near a lower part of the cryostat 2 in a similar way to that in FIG. 11. As described in connection with FIG. 11, with the construction shown in FIG. 12, the fore end surface of the ultrasonic transducer probe 8 can be brought into intimate contact to the body surface 29 at a desired position in the circumferential direction of the cryostat 2.

In the foregoing description, the ultrasonic transducer probe shown in FIG. 10E for performing mechanical scanning is described as being mounted to the gantry 180 exemplarily but the ultrasonic transducer probe as shown in FIGS. 10A, 10B, 10C, 10D or 10E, comprised of the one-dimensional or two-dimensional array transducer used in the shielded room, can also be provided to part of the gantry 180.

Figure 13:
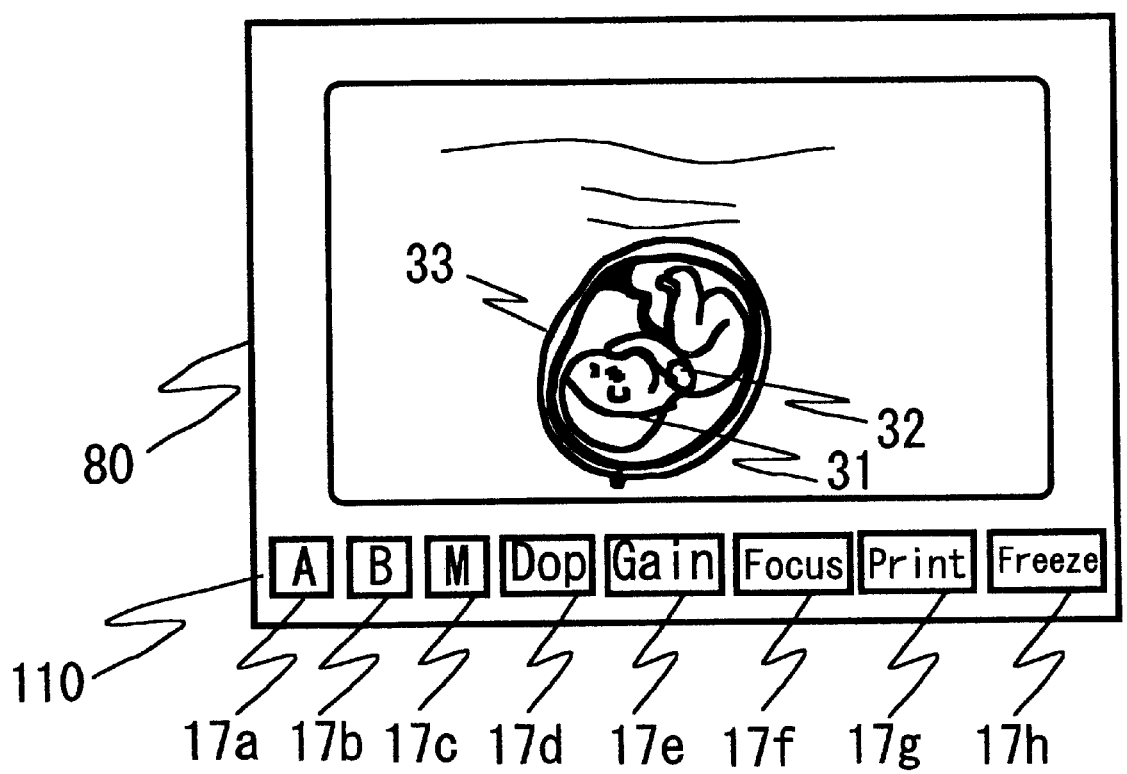
FIG. 13 is a diagram for explaining the construction of a monitor display in the embodiment of the present invention.

FIG. 13 is a diagram for explaining the construction of the monitor display 80 in the embodiment of the present invention. The monitor display 80 has a controller 110 and a display screen. Ultrasonic images in modes set by setting buttons 17a to 17d for various kinds of measurement (photographing) can be displayed. Modes are settable by using the A mode setting button 17a (button A in FIG. 13) for permitting estimation of impedance at individual portions of the living body, the B mode setting button 17b (button B in FIG. 13) adapted to obtain an ultrasonic cross-sectional image, the M mode setting button 17c (button M in FIG. 13) for permitting observation of temporal motion of the wall surface of a tissue, and the Doppler mode or CFM mode setting button 17d (button Dop in FIG. 13) for permitting monitoring of motion of blood flow. Any one of the A mode, M mode and Doppler mode or CFM mode is operative alternately with the B mode.

The ultrasonic image can be adjusted by means of a gain adjusting button 17e (button Gain in FIG. 13) and a focus adjusting button 17f (button Focus in FIG. 13) so that a clear image may be obtained. When the ultrasonic image is desired to be printed out, a freeze button 17h (button Freeze in FIG. 13) is depressed to temporarily stop the picture and then a print starting button 17g (button Print in FIG. 13) is depressed, so that a temporarily stopped ultrasonic image can be printed. In the foregoing description, the ultrasonic image is displayed on the monitor display 80 but display data is not limited to the ultrasonic image and for example, a waveform of electrocardiogram and waveforms of the cardiac magnetic field obtained with the SQUID magnetometers can also be displayed at the same time.

Preferably, the monitor display 80 is constructed of a liquid display or a plasma display which generates less magnetic field noise. Each of the various kinds of buttons 17a to 17h of the monitor display 80 may be constructed to be part of a touch panel or may have the function of a lighting display so as to act as a display lamp which indicates a lighting display of a mode of ultrasonic image controlled by the controller 110 provided separately from the monitor display 80.

Figure 14:
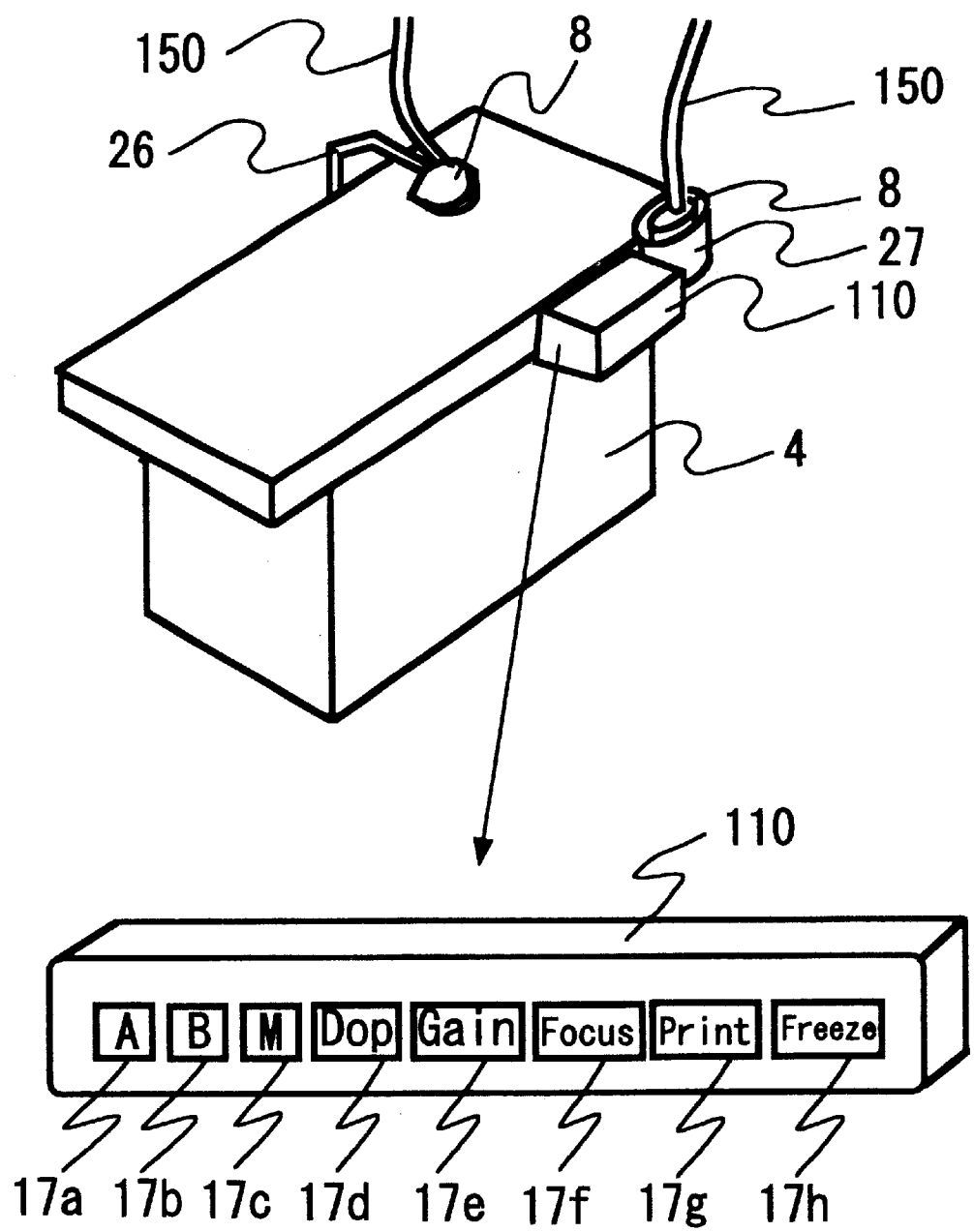
FIG. 14 is a perspective view for explaining the arrangement of a control part and ultrasonic transducer probe holding members of the ultrasonic diagnosis apparatus an embodiment of the present invention.

FIG. 14 is a diagram for explaining a control part and an ultrasonic probe holding stage of the ultrasonic diagnosis apparatus as part of an embodiment of the present invention. The controller 110 of the ultrasonic diagnosis apparatus can be a handheld type controller which is normally arranged by the side of the bed 4 and which can be detached from the bed 4 as necessary. Control by the controller 110 is similar to that in FIG. 13 and can be executed by selecting any of the setting buttons 17a to 17d for various kinds of measurement (photographing) modes, the gain adjusting button 17e, the focus adjusting button 17f, the freeze button 17h and the print starting button 17g.

The controller 110 shown in FIG. 14 and the ultrasonic diagnosis apparatus main body 6 shown in FIG. 7 are connected together by communication means utilizing infrared rays, or are electrically interconnected by a cable, and various kinds of data including control signals and image data are interchanged between the controller 110 and the ultrasonic diagnosis apparatus main body 6. The contents of control by the controller 110 is lit and displayed on the display screen of the monitor display 80 of FIG. 13. Ultrasonic transducer probe holding members 26 and 27 are arranged by the side of the bed 4. When the operator performs measurement by the ultrasonic diagnosis apparatus concurrently with cardiac magnetic field measurement, the ultrasonic transducer probe holding member 26 is adjusted such that the ultrasonic transducer probe 8 is brought into contact with a part of the inspected subject at a position where the ultrasonic transducer probe does not contact the cryostat 2, and is fixed such that the part to be measured is encompassed in the view field.

When the cardiac magnetic field measurement and the measurement by the ultrasonic diagnosis apparatus need not be carried out at the same time, the ultrasonic transducer probe 8 is temporarily placed on the ultrasonic transducer probe holding member 27 disposed by the side of the bed 4, and thereafter measurement by the ultrasonic diagnosis apparatus can be executed as necessary. Additionally, the setting buttons 17a to 17d for various kinds of measurement (photographing) modes, the gain adjusting button 17e, the focus adjusting button 17f, the freeze button 17h and the print starting button 17g may be provided externally of the ultrasonic transducer probe 8.

Figure 15:
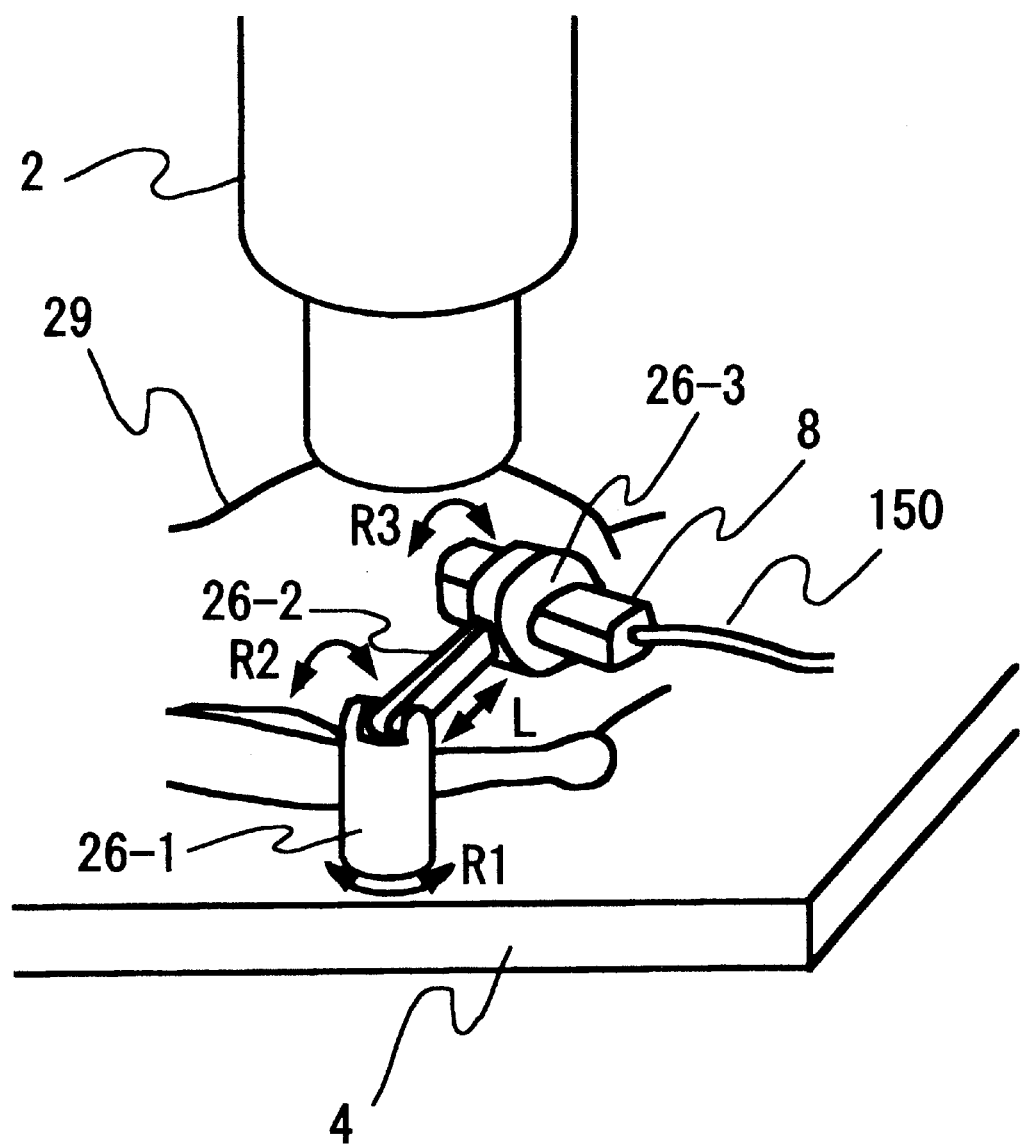
FIG. 15 is a perspective view for explaining details of the construction of the ultrasonic transducer probe holding member an embodiment of the present invention.

FIG. 15 is a diagram for explaining details of construction of the ultrasonic transducer probe holding member 26. The main shaft of rotational axis member 26-1 is rotatably (in $R_1$ direction) connected vertically to the surface of the bed 4, one end of arm member 26-2 having a telescopic mechanism for making the length in the longitudinal direction (L direction) variable is rotatably (in $R_2$ direction) connected to the main shaft of the rotational axis member 26-1 and a member 26-3 for holding the ultrasonic transducer probe 8 is rotatably (in $R_3$ direction) connected to the other end of the arm member 26-2. By adjusting rotations in the $R_1$, $R_2$ and $R_3$ directions and the length in the L direction, the fore end surface of the ultrasonic transducer probe 8 can be brought into intimate contact with the body surface 29.

As described above, according to the present invention, when a magnetic field generated from the heart of a subject to be inspected (adult or foetus) is measured, the operator can observe the position of the heart of the inspected subject on a substantially real time basis by watching an ultrasonic tomographic image inside the shielded room and hence, the SQUID magnetometers can be quickly positioned to optimum measuring positions and the magnetic field generated from the heart of the inspected subject can be detected clearly with high sensitivity. Further, the bottom surface position of the cryostat 2 can be brought into intimate contact with the body surface by so adjusting the magnetic field signal from the heart of the foetus as to be maximized while observing the position of the heart of the foetus through an ultrasonic tomographic image, thereby ensuring that measurement of the magnetic signal from the heart of the foetus, and at the same time observation of the blood flow state in the heart, can be carried out inside the shielded room.

What is claimed is:

1. A biomagnetic field measurement apparatus comprising:

a shielded room;

a bed which is adapted to hold a subject to be inspected in said shielded room;

a cryostat in which a plurality of SQUID magnetometers are arranged at low temperature, wherein said cryostat is arranged in said shielded room and the plurality of SQUID magnetometers detect a normal component of a magnetic field generated from a heart of a fetus in said subject to be inspected;

a gantry which is adapted to hold said cryostat, and which is arranged in said shielded room;

a driving and detecting circuit which drives the plurality of SQUID magnetometers and detects signals from the plurality of SQUID magnetometers;

an electrocardiograph which is used to obtain an electrocardiogram of said subject to be inspected, wherein the measure of said electrocardiogram and the measurement of the normal component of said magnetic field are carried out simultaneously;

a computer which collects the signals from said driving and detecting circuit and collects signals from said electrocardiograph, and processes the signals from said driving and detecting circuit to obtain a magnetic field waveform expressing a temporal change of said magnetic field, and to obtain a distribution of the magnetic field in the heart of the fetus and a distribution of an electric current in the heart of the fetus, wherein said computer calculates said distribution of the magnetic field by an equation of $\sqrt{(dB_z/dx)^2+(dB_z/dy)^2}$, where (x, y, z) are Cartesian coordinates and $B_z$ is said normal component of said magnetic field, and calculates said distribution of the electric current by 90° counterclockwise rotation of a vector of the differential values $(dB_z/dx, dB_z/dy)$; and a display which displays said magnetic field waveform and which is arranged in said shielded room such that an operator positioning a lower surface of said cryostat with respect to said subject to be inspected can observe said magnetic field waveform on said display.

2. A biomagnetic field measurement apparatus comprising:

a shielded room;

a bed which is adapted to hold a subject to be inspected in said shielded room;

a cryostat in which a plurality of SQUID magnetometers are arranged at low temperature, wherein said cryostat is arranged in said shielded room and the plurality of SQUID magnetometers detect a magnetic field generated from a heart of a fetus in said subject to be inspected, and a lower surface of said cryostat is arranged near or on a surface of the lower abdomen of said subject to be inspected;

a gantry which is adapted to hold said cryostat in said shielded room;

a driving and detecting circuit which drives the plurality of SQUID magnetometers and detects signals from the plurality of SQUID magnetometers;

a computer which collects the signals from said driving and detecting circuit and which processes the signals from said driving and detecting circuit to obtain a magnetic field waveform expressing a temporal change of said magnetic field;

an ultrasonic transducer probe arranged in said shielded room;

a main body of an ultrasonic diagnosis apparatus which comprises a transmitting circuit and a processor, and which is arranged outside of said shielded room, wherein said transmitting circuit drives said ultrasonic transducer probe and said ultrasonic transducer probe transmits an ultrasound wave to the heart of the fetus of said subject to be inspected, and said processor processes reflected ultrasound waves from the heart of the fetus, to obtain an ultrasonic image of the fetus, and said reflected ultrasound waves are received by said ultrasonic transducer probe;

a probe holder which is adapted to hold said ultrasonic transducer probe and to bring a surface of said ultrasonic transducer probe into contact with the surface of the lower abdomen of said subject to be inspected, and which is arranged on said bed or said gantry; and a display which is arranged in said shielded room and displays said ultrasonic image of the fetus.

3. A biomagnetic field measurement apparatus comprising:

a shielded room;

a bed which is adapted to hold a subject to be inspected in said shielded room;

a cryostat in which a plurality of SQUID magnetometers are arranged at low temperature, wherein said cryostat is arranged in said shielded room, and the plurality of SQUID magnetometers detect a normal component of a magnetic field generated from a heart of a fetus in said subject to be inspected, and a lower surface of said cryostat is arranged near or on a surface of the lower abdomen of said subject to be inspected;

a gantry which is adapted to hold said cryostat in said shielded room;

a driving and detecting circuit which drives the plurality of SQUID magnetometers and detects signals from the plurality of SQUID magnetometers;

a computer which collects the signals from said driving and detecting circuit and which processes the signals from said driving and detecting circuit to obtain a magnetic of the magnetic field in the heart of said fetus in said subject to be inspected, wherein said computer calculates said distribution of the magnetic field by an equation of $\sqrt{(dB_z/dx)^2 + (dB_z/dy)^2}$, where (x, y, z) are Cartesian coordinates and $B_z$ is said normal component of said magnetic field; and a display which is arranged in said shielded room and displays said distribution of the magnetic field.

* * * * *